(12) United States Patent
Vervaet et al.

(10) Patent No.: US 7,264,826 B2
(45) Date of Patent: Sep. 4, 2007

(54) PHARMACEUTICAL COMPOSITIONS OF CELL LYSATE AND PROCESSES FOR THE PRODUCTION AND USE THEREOF

(75) Inventors: Chris Vervaet, Izegem (BE); Jean-Paul Remon, Melle (BE); Bernard Delaey, Zingem (BE); Peter De Waele, Lochristi (BE)

(73) Assignee: CellTran Limited, Sheffield (GB)

( * ) Notice: Subject to any disclaimer, the term of this patent is extended or adjusted under 35 U.S.C. 154(b) by 0 days.

(21) Appl. No.: 10/537,301

(22) PCT Filed: Nov. 25, 2003

(86) PCT No.: PCT/EP03/50891

§ 371 (c)(1),
(2), (4) Date: Jun. 2, 2005

(87) PCT Pub. No.: WO2004/050121

PCT Pub. Date: Jun. 17, 2004

(65) Prior Publication Data

US 2006/0039989 A1    Feb. 23, 2006

Related U.S. Application Data

(60) Provisional application No. 60/433,912, filed on Dec. 17, 2002.

(30) Foreign Application Priority Data

Dec. 3, 2002    (EP)    ................................ 02447238

(51) Int. Cl.
*A61K 35/12*    (2006.01)
(52) U.S. Cl. .................................... 424/520
(58) Field of Classification Search ................ 424/520, 424/572; 435/325
See application file for complete search history.

(56) References Cited

U.S. PATENT DOCUMENTS

| | | |
|---|---|---|
| 3,956,519 A | 5/1976 | Evans et al. |
| 4,565,635 A | 1/1986 | Le Du et al. |
| 5,387,415 A | 2/1995 | Wunderlich et al. |
| 5,804,213 A * | 9/1998 | Rolf ............................ 424/445 |
| 5,866,167 A | 2/1999 | Van Bossuyt |
| 6,010,719 A | 1/2000 | Remon et al. |
| 6,046,178 A | 4/2000 | Silvetti, Sr. |
| 6,126,935 A | 10/2000 | Van Bossuyt |
| 6,585,969 B1 | 7/2003 | Van Bossuyt |
| 2005/0079147 A1 | 4/2005 | Delaey et al. |

FOREIGN PATENT DOCUMENTS

| | | |
|---|---|---|
| JP | 7-267876 | 10/1995 |
| WO | WO95/01782 | 1/1995 |
| WO | 97/41899 | 11/1997 |

OTHER PUBLICATIONS

Hodge et al, "Flocculation or Bacteria by Hydrophilic Colloids", Aug. 29, 1957, vol. 75, pp. 258-264.
Tempio et al, J. Pharm. Sci., Oct. 1980; 69(10):1209-14 (Abstract).
Vanapalji et al, Journal of Agricultural and Food Chemistry 50 (18):5224-5228 Aug. 28, 2002 (Abstract).
Ye et al, Journal of Agricultural and Food Chemistry 52 (17):5491-5498, Aug. 25, 2004 (Abstract).
Zatz et al, International Journal of Pharmaceutics, vol. 9, Issue 4, Oct. 1981, pp. 315-319 (Abstract).
Velez et al, Journal of Agricultural and Food Chemistry 51(1):265-269, Jan. 1, 2003 (Abstract).
Quintana et al, Journal of Texture Studies 33(3):215-236, Sep. 2002 (Abstract).
Hemar et al, Food Hydrocolloids 15(4-6):513-519, Jul.-Nov. 2001 (Abstract).
Singh et al, Current Science 78(7):798-803, Apr. 10, 2000 (Abstract).
Koczo et al, Food Hydrocolloids 12(1):43-53, Jan. 1998 (Abstract).
Zatz et al, International Journal of Pharmaceutics 9(4):315-319, 1981 (Abstract).
Walkenstrom et al "Effects of fluid shear and temperature on whey protein gels, pure or mixed with xanthan", Food Hydrocolloids 12 (1998) 469-479.
Press Release—"43% relative improvement versus control group in hard-to-heal venous leg ulcers obtained with XCELLentis' LyphoDerm™" Gent (Belgium), Mar. 2, 2004 (printed from URL: innogenetics.com/site/pressview.asp?id=125&lang=E on Feb. 13, 2007).

* cited by examiner

*Primary Examiner*—Sandra E. Saucier
*Assistant Examiner*—Satyendra K. Singh
(74) *Attorney, Agent, or Firm*—Nixon and Vanderhye P.C.

(57) ABSTRACT

The present invention relates to a pharmaceutical composition comprising a non-viable cell lysate and at least one antiflocculant and/or antisedimentation agent(s). The pharmaceutical composition of the present invention comprising the cell lysate is in the form of a solution or a suspension or a lyophilisate, in particular, the homogenized cell lysate compositions are in the form of solutions or suspensions or lyophilisates. The present invention further discloses processes for the production and the use of the pharmaceutical composition.

10 Claims, No Drawings

PHARMACEUTICAL COMPOSITIONS OF CELL LYSATE AND PROCESSES FOR THE PRODUCTION AND USE THEREOF

This application is the US national phase of international application PCT/EP2003/050891 filed 25 Nov. 2003, which designated the U.S. and claims benefit of EP 02447238.3 filed 3 Dec. 2002, and U.S. Provisional Application No. 60/433,912 filed 17 Dec. 2002, the entire contents of each of which are hereby incorporated by reference.

FIELD OF THE INVENTION

The present invention relates to a pharmaceutical composition comprising a non-viable cell lysate and at least one antiflocculant and/or antisedimentation agent(s). The pharmaceutical composition of the present invention comprising the cell lysate is in the form of a solution or a suspension or a lyophilisate, in particular, the homogenized cell lysate compositions are in the form of solutions or suspensions or lyophilisates. The present invention further discloses processes for the production and the use of the pharmaceutical composition.

BACKGROUND OF THE INVENTION

In the production of a pharmaceutical composition of non-viable cell preparations in the form of a solution or a suspension, such as cell lysates, problems are often encountered with aggregation, flocculation and/or sedimentation. This problem causes inhomogeneity in the product, leading to qualitative or quantitative inconsistencies, particularly in case the product has to be dispensed over multiple containers. In addition, it may cause lack of homogeneity between multiple batches of the product.

For example, in the production of a wound healing composition such as a keratinocyte cell lysate, and in particular cultured human keratinocyte cell lysates, rapid aggregation, flocculation and partial sedimentation of the cell lysate contained in these solutions or suspensions is observed after the homogenization (lysis) steps in the production process. Such aggregation, flocculation and/or sedimentation results in lack of homogeneity in the solution or suspension of the cell lysate and further complicates its processing, in some cases, this can even render the composition unusable for its intended purpose. Thus there is a need for modifications that can aid the processing step before or after homogenization by preventing flocculation or sedimentation.

It is well known that chemical agents stimulate flocculation or aggregation of proteins leading to precipitation. U.S. Pat. No. 4,565,635 describes a water soluble chemical agent "xanthan gum", known to function as a flocculating adjuvant Similarly U.S. Pat. No. 3,956,519 describes a process in which aggregation of a protein in aqueous solution is induced by dissolved debranched low-DE maltodextrin or debranched amylopectin.

In the pharmaceutical sector, xanthan gum is utilized in the manufacturing of freeze dried pharmaceutical tablets as described in the WO Application No. 9501782 in which xanthan gum facilitates suspension of the granular therapeutic agents in the liquid admixture and does not have any adverse affects on the dispersion qualities and texture of the tablet upon usage.

On the contrary U.S. Pat. No. 6,010,719 describes use of xanthan gum as a thickening agent, which increases viscosity of the suspension and is suitable for preventing sedimentation of the solid drug particles. Similarly, xanthan gum has also been used to suspend large biological particles for the purpose of stabilizing cell suspensions during flow cytometry, thereby preventing sedimentation (Cytometry 10: 803-806 (1989)). Another example shows that the presence of xanthan inhibited the aggregation and demixing of whey protein isolates and resulted in a homogenous mixture (Food Hydrocolloids 12: 469-479 (1998)).

All these examples however apply to relatively simple intact suspensions of cells or specific proteins.

Cell lysates, on the other hand, result from the lysis of cells, which releases many components in various forms, forming an extremely complex mixture of constituents such as proteins, glycoproteins, polysaccharides, lipids, nucleic acids etc. All these components may interact with each other, significantly increasing the possibility for complex formation and flocculation, ultimately resulting in a non-stable solution or suspension and sedimentation of part of these components.

Accordingly, it can be seen that there remains a need to provide a homogenous stable pharmaceutical composition comprising cell lysates. One example of such a composition contains a keratinocyte cell lysate, which is suitable for wound healing purposes. There further remains a need to provide such pharmaceutical composition of cell lysates in the form of a solution or a suspension, which are homogenized and if required further processed by drying or freeze-drying.

SUMMARY OF THE INVENTION

The present invention relates to a pharmaceutical composition comprising a cell lysate and at least one antiflocculant and/or antisedimentation agent(s).

The present invention further provides a homogeneous pharmaceutical composition in a dried or freeze-dried form.

The present invention provides a pharmaceutical composition comprising a cell lysate and at least one antiflocculant and/or antisedimentation agent(s), wherein the antiflocculant/antisedimentation agent is xanthan gum.

The present invention further provides a pharmaceutical composition, in which the antiflocculant and/or antisedimentation agent is a combination of xanthan gum and maltodextrin.

Further, the pharmaceutical composition may comprise a buffering agent. Examples of buffers which are useful in this regard, include citrate buffers, phosphate buffers, or any other suitable buffer known in the art preferably clinically acceptable buffering agents.

The present invention further provides a process for the production of a pharmaceutical composition of cell lysate in the form of a solution or a suspension that is substantially free of inconsistencies. An example of such a pharmaceutical composition is a homogeneous freeze-dried pharmaceutical composition of a keratinocyte cell lysate.

The present invention also provides processes for the production of a homogenized, sterilized composition of a keratinocyte cell lysate in the form of a solution or a suspension.

The pharmaceutical composition of the present invention may be useful for various therapeutic applications and may further comprise a pharmaceutically acceptable carrier or vehicle or recipient One example is a composition of keratinocyte cell lysate useful in the treatment of wounds such as burn wounds or skin ulcers.

The present invention provides a pharmaceutical composition for promoting the healing of a wound; wherein said composition comprises a non-viable keratinocyte lysates and a pharmaceutically acceptable vehicle. The said pharmaceutically acceptable vehicle is a dry powder, suspension or solution. Further in this regard, the said pharmaceutically acceptable vehicle is a gel, cream, ointment or a biocompatible matrix other than a gel.

The present invention also provides a process for treating a surface wound to promote healing in a mammal comprising the step of:
(a) applying to said surface wound the pharmaceutical composition; and
(b) promoting healing of said surface wound.

The present invention disclosed herein is a pharmaceutical composition of cell lysate in the form of a solution or a suspension, or a freeze-dried form thereof, further characterized in that it is substantially free of inconsistencies. This solution or suspension of the cell lysate or the freeze-dried form thereof comprises xanthan gum and/or maltodextrin that acts as an anti-flocculant agent(s) for preventing the formation of flocculants in the solution or suspension that may sediment.

The present invention discloses a process for the production of a homogenized pharmaceutical composition comprising the steps of growing, lysing and drying the cells, which process is characterized in that, immediately after lysing, antiflocculant and/or antisedimentation agents are added to stabilize the cell lysate mixture. The said agent is xanthan gum or combination of xanthan gum and maltodextrin which prevents the formation of flocculants that may sediment in the solution or suspension. Furthermore, this process may optionally include the freeze-drying or otherwise drying of the solution or suspension to obtain a water-free product.

DETAILED DESCRIPTION OF THE INVENTION

A pharmaceutical composition of the present invention is a composition of cell lysate in the form of a solution or a suspension. These pharmaceutical compositions containing a cell lysate further comprise a buffer component and at least one anti-flocculant and/or anti-sedimentation agent These compositions may be further processed by freeze-drying or otherwise drying, resulting in a substantially water-free product with even better long-term stability.

Within the context of this invention, the term "inconsistencies" refers to the situation where the composition of the cell lysate is not homogeneous, in such a way that the composition of one part of the lysate may differ from the composition of another part of the lysate.

The term "cell lysate" refers to non-viable cell suspensions or fractions thereof; obtained by lysing the cells. The cell lysate in the solution or suspension of the present invention may be whole cells, parts of cells or any fractions or mixtures thereof obtained after a lysis step.

The cell lysate may be obtained by any of the various processes which are well-known to those skilled in the art. For example, whole cells may be obtained as described in U.S. Pat. No. 6,126,935. Parts of cells may be obtained by lysing whole cells, subjecting the resulting lysate to centrifugation wherein certain parts of the resulting cell lysate are in the pellet fraction and certain other parts of the resulting cell lysate are in the supernatant and only one of the two parts are used. An example of such a process is disclosed in U.S. Pat. No. 6,126,935.

The term "cell lysis" refers to any type of cell (i.e. prokaryotic or eukaryotic) and involves the action of rupturing the cell wall and/or the cell membrane of cells (present in the form of solution or suspension) subjected to a treatment which may include chemical, biological, mechanical or thermal treatment, possibly resulting in the release of its biological constituents.

Numerous mechanical methods for lysis have been developed and published. They include pressure, cavitation, sonic or ultrasonic waves, mechanical shaking or grinding (Sadeva, Biopharm 7(2):26-36, 1994).

Cell lysates may be obtained by mechanically homogenizing the cells. The Keratinocyte cell lysates of the present invention may preferably be obtained by a process as described in U.S. Pat. No. 6,126,935.

It should be understood that the term "homogenization or homogenizing" used in the present context denotes the processing of the cell lysate mixture by making the said mixture homogeneous in such a way as to ensure that any given part of the above mentioned mixture has the same composition and physico-chemical properties as any other part of that same mixture. The term homogenization or homogenizing may also refer to lysis in the sense that certain homogenization procedures also lead to cell lysis.

The concentration of cell lysate in a composition of the present invention varies according to the type of cell lysate in the composition, as well as according to its intended use. In this regard, the concentration of cell lysate ranges from 0.02 to 5% w/v (percentage refers to weight percentage of total protein in the cell lysate, as determined by a suitable protein quantification assay). Preferably, the concentration of the cell lysate ranges from 0.05 to 2% w/v. More preferably, the concentration of the cell lysate ranges from 0.1 to 1% w/v.

The liquid component of the solutions/suspensions of the present invention may be any liquid suitable for supporting the cell lysate in the solution or suspension. Examples of such liquid components are water, oil, or emulsions (such as water-in-oil or oil-in-water emulsions) and other similar liquids.

In cases involving a pharmaceutical composition of keratinocyte cell lysates of the present invention, the use of an isotonic solution of sodium chloride (for osmotic adjustment), phosphate buffer and lysed cells is contemplated Preferably, this is supplemented with a solution of a lyoprotectant (such as sucrose, maltodextrin, glycine, sorbitol, trehalose, polyvinylpyrrolidone, polyethylene glycol or any other suitable lyoprotectant or combination thereof) and a citrate buffer (such as sodium citrate) for aiding the subsequent freeze-drying of the composition.

A pharmaceutical composition of the present invention in addition may contain other buffers or buffer systems. Examples of such buffers may include phosphate, citrate or any other compositions, which can act as a pH-buffer.

In a particular embodiment, the present invention involves a pharmaceutical composition obtained by a process comprising the step of lysing the cells prior to adding at least one anti-flocculant and/or anti-sedimentation agent to the composition of a non-viable cell lysate solution or suspension.

In a particular embodiment, the present invention provides a pharmaceutical composition comprising a cell lysate and antiflocculant and/or antisedimentation agent(s), wherein the antiflocculant/antisedimentation agent is xanthan gum Xanthan gum may be obtained commercially or by fermentation. The concentration of xanthan gum in the pharmaceutical composition of cell lysate of the present invention will range from 0.001 to 5% w/v, more preferably 0.01 to 1% w/v, most preferably 0.05 to 0.5% w/v.

In a particular embodiment the present invention involves a pharmaceutical composition of keratinocyte cell lysate, the use of xanthan gum aids in preventing flocculation and sedimentation in the keratinocyte cell lysate solution or suspension prior to or during use or further processing. Accordingly, the formation of inconsistencies in the solution or suspension is avoided. This facilitates further processing and use of the keratinocyte cell lysate solution or suspension for the formation of a composition useful in wound healing, for example, for the treatment of skin ulcers or burns.

In a particular embodiment, the present invention provides a pharmaceutical composition comprising a cell lysate and antiflocculant and/or antisedimentation agent(s), wherein the antiflocculant/antisedimentation agent is maltodextrin.

The concentration of maltodextrin in the solutions/suspensions of the present invention may range from 0.01 to 10% w/v. Alternatively; a concentration of maltodextrin ranging from 0.5 to 2% w/v may be used.

In this regard, it is noted that in certain circumstances, it is desirable for the composition of the present invention to have a particular pH and/or be maintained within a specific pH range. For example, for a pharmaceutical composition of keratinocyte cells of the present inventions, it is preferred to maintain the composition at a pH of substantially 6.8.

Accordingly, a buffer is employed for this purpose. Examples of buffers which are useful in this regard, include citrate buffers, phosphate buffers, or any other suitable buffer known in the art, preferably also clinically acceptable. The precise concentration of buffer to include in the final solution or suspension will vary according to various factors including the strength of the buffer and the pH, which is required for the composition. Nonetheless, it is contemplated herein that, where keratinocyte lysate suspensions are involved, the final concentration of buffer in the composition of the invention will range from 5 to 200 mM, preferably from 10 to 100 mM, more preferably from 20 to 50 mM. This can be achieved by adding a concentrated buffer stock solution, for instance with a concentration of approximately 1500 mM, to the composition.

In the event the pharmaceutical compositions and particularly if the solutions/suspensions of the present invention are to be dried or freeze-dried, they may further include sucrose.

The concentration of sucrose in the composition of the present invention will vary according to the type of composition, as well as according to the use to which the composition will be placed. In this regard, the concentration of sucrose ranges from 1 to 30% w/w, preferably from 2 to 20% w/w, more preferably from 5 to 10% w/w. This can be achieved by adding sucrose powder or a concentrated sucrose stock solution, for instance with a concentration of approximately 50%, to the composition. It will be clear that instead of sucrose, a suitable concentration of another lyoprotectant may also be used, such as glycine, trehalose, sorbitol, polyvinyl pyrrolidone, polyethylene glycol or any other suitable lyoprotectant or combination thereof known in the art.

The pharmaceutical composition of the present invention may further include such other and different ingredients as may be desirable for the particular cell lysate implicated and/or use for which the composition is intended.

It is possible that the solutions/suspensions of the present invention may further include additional components, some of which being a consequence of obtaining the biological (cellular) material. Examples of such ingredients include proteins, culture media, washing media and other organic and/or inorganic material that has a tendency to flocculate and/or sediment or provoke the flocculation and/or sedimentation of the other constituents.

The precise concentration of these additional components may vary greatly depending upon the composition, the use to which the composition will be placed and the precise additional component in question.

In a particular embodiment, the present invention involves a process for the production of a homogenized pharmaceutical composition comprising the steps of growing, lysing and drying the cells, which process is characterized in that, immediately after lysing, antiflocculant and/or antisedimentation agents are added to stabilize the cell lysate mixture.

In a particular embodiment, the present invention involves a process for the production of a homogenized pharmaceutical composition comprising the steps of growing, lysing and drying the cells, which process is characterized in that, immediately after lysing, xanthan gum is added as a antiflocculant and/or antisedimentation agent to stabilize the cell lysate mixture.

In a particular embodiment, the present invention involves a process for the production of a homogenized pharmaceutical composition comprising the steps of growing, lysing and drying the cells, which process is characterized in that, immediately after lysing, a mixture of xanthan gum and maltodextrin is added as antiflocculant and/or antisedimentation agents to stabilize the cell lysate mixture.

In a particular embodiment, the present invention involves a process for the production of various pharmaceutical compositions of biological materials in the form of a solution or a suspension or freeze-dried solution or suspension, including compositions used to produce a composition of cell lysate in the form of a solution or a suspension or freeze-dried solution or suspension. Of particular utility is the use of the process of the present invention to produce a composition of keratinocyte cell lysate in the form of a solution or a suspension or freeze-dried solution or suspension.

The solution or suspension is formed by combining (such as, for example, by mixing) the cell lysate, obtainable by any process known to those skilled in the art with one or more suitable excipients, possibly in a liquid form. This may be achieved by any process well known to those skilled in the art, which is suitable for use with the particular biological material and/or liquid component involved. It is anticipated herein (and as was discussed above), particularly in cases wherein a keratinocyte cell lysate is involved, that the solution or suspension of cell lysate will be formed by obtaining the cell lysate and the excipients (possibly in liquid form), either individually or at the same time, and mixing the cellular matter with the excipients in such a manner that a solution or a suspension of the cell lysate is formed.

The keratinocyte cell lysate may be prepared in the form of an isotonic solution of sodium chloride 0.9% (w/w), phosphate-buffered saline or any other suitable medium. The cell lysate is then homogenized mechanically and may be stored if required at $-70°$ C. The frozen homogenate is then thawed and supplemented with the addition thereto of the excipients comprised of sucrose to a final concentration of 6.5% (as a lyoprotectant) and citrate buffer to a final concentration of 30 mM The concentration of cell lysate and the liquid component to be added to the composition in the process of the present invention will vary according to the type of cell lysate in the composition, as well as according to its intended use.

Adding the xanthan gum to the suspension or solution of cell lysate may be performed in any suitable manner well-known to those skilled in the art. For example, this may be done by adding the xanthan gum in its solid state to the solution or suspension under conditions which facilitate its dissolution and homogeneous distribution throughout the solution or suspension or it may be first dissolved in a liquid, such as water, before being added to the suspension/solution of cell lysate. As was noted above, the addition of this xanthan gum, immediately after the homogenization still permits the xanthan gum to exercise its anti-flocculation/anti-sedimentation properties without subjecting the xanthan gum to the homogenization process which negatively impacts its viscosity properties.

In a particular embodiment, the process for the production of a composition of cell lysate that is in the form of a solution or a suspension of the present invention may further comprise homogenization of the formed composition of cell lysate of the present invention prior to the adding of the xanthan gum thereto.

Homogenization may be performed by using any known suitable homogenization techniques which is well known to those skilled in the art, including mechanical and chemical processes, and under such process conditions as is needed to lyse the cells as needed.

Of particular importance in this regard for keratinocyte lysate solutions/suspensions is homogenizing the solution or suspension by high-pressure homogenization. Such homogenization may be conducted using any appropriate apparatus, such as a cell breaker (Constant systems, U.K.). In this particular embodiment, homogenization is conducted at a pressure of 2000 bar between 4 and 20° C. The result is a cell lysate in the form of a suspension. In this regard, it is noted that traditionally, anti-flocculants are added to compositions of cell lysate before homogenization This is done for ease of processing and to help prevent flocculation during homogenization. However, this also may negatively impact on the viscosity properties of the anti-flocculant, especially in case xanthan gum is used as an antiflocculant, resulting in inconsistencies forming in the composition.

Surprisingly, we have found herein that, the presence of an anti-flocculant agent and/or anti-sedimentation agent in the composition is not needed before homogenization. We have found that should the anti-flocculant agent and/or anti-sedimentation agent be added to the composition immediately after the (high-pressure) homogenization, flocculation in the composition is still substantially prevented while the viscosity properties of the anti-flocculant are not negatively impacted.

The process for the production of a composition of cell lysate that is in the form of a solution or a suspension of the present invention may further be comprised of adding a citrate buffer and/or sucrose (both being obtained as described above) to the compositions of cell lysate of the present invention in concentrations, as were also set forth above.

As disclosed herein, the compositions and the processes of the present invention are of particular application in and of particular interest to the formation of a pharmaceutical composition of keratinocyte cell lysates that are in the form of a solution or a suspension.

In this regard, keratinocyte cell lysates may be obtained as described in U.S. Pat. No. 6,126,935.

In a particular embodiment, disclosed herein is a pharmaceutical composition of cell lysates in the form of solutions or suspensions and, more particularly keratinocyte cell lysate in the form of a solution or a suspension, or freeze-dried forms thereof at concentrations ranging from 0.2-50 mg/ml, preferably 5-20 mg/ml, more preferably 1-10 mg/ml (the concentrations provided refer to the concentration of protein within the lysate). These solutions/suspensions of cell lysate include xanthan gum that acts as an anti-flocculant agent for preventing the formation of flocculants that may sediment in the solution or suspension. The final concentration of xanthan gum in the pharmaceutical composition (in form of solution or suspension) of the cell lysate of the present invention will range from 0.001 to 5% w/v, more preferably 0.01 to 1% w/v, most preferably 0.05 to 0.5% w/v.

In a particular embodiment, the pharmaceutical composition of cell lysate of the present invention may further include maltodextrin that acts as an anti-flocculant agent for preventing the formation of floccules that may sediment within the solution or suspension.

In one embodiment, the final concentration of maltodextrin in a pharmaceutical composition of cell lysate of the present invention may range from 0.01 to 10% w/v, more preferably 0.1 to 5% w/v most preferably 0.5 to 2% w/v.

In another embodiment, a pharmaceutical composition of cell lysate of the present invention may further include a citrate buffer and/or sucrose.

In a particular embodiment, a pharmaceutical composition of cell lysate of the present invention may further include an excipient and, in particular, a gel-forming excipient.

In a particular embodiment of the present invention, the composition of cell lysate of the present invention is homogenized.

In another particular embodiment of the present invention, the homogenized composition is father processed by drying. Drying may be performed in various ways known in the art, such as evaporation, vacuum-drying, spray drying, fluidized bed drying, infrared drying, microwave drying or otherwise removing the water present in the solution or suspension, as long as the drying process does not negatively impact the properties of the final composition. One of the many preferred methods for removing the water is by freeze-drying.

In a particular embodiment of this aspect of the present invention, the process of the present invention is used to produce a composition of cell lysate in the form of a solution or a suspension and, more particularly, a composition of keratinocyte cell lysate in the form of a solution or a suspension, possibly in a dried form.

In one embodiment, the final concentration of xanthan gum added to the pharmaceutical composition of cell lysate of the present invention may range from 0.001 to 5% w/v. In another embodiment, the concentration of xanthan gum may range from 0.05 to 0.5% w/v.

In a particular embodiment, the process for the production of a composition of cell lysate that is in the form of a solution or a suspension of the present invention may further include adding maltodextrin to the composition of cell lysate, whereby the maltodextrin acts as an anti-flocculant agent for preventing the formation of flocculants that may sediment within the solution or suspension.

In a particular embodiment, the final concentration of maltodextrin added to a pharmaceutical composition of cell lysate of the present invention may range from 0.01 to 10% w/v. For most applications, a concentration of maltodextrin ranging from 0.5 to 2% w/v may be adequate.

In a particular embodiment, the present invention involves a process for the production of a homogenized pharmaceutical composition comprising the steps of growing, lysing and drying the cells, which process is characterized in that, immediately after lysing by a high-pressure homogenization, a mixture of xanthan gum and/or maltodextrin are added as a antiflocculant and/or antisedimentation agents to stabilize the cell lysate mixture.

In a particular embodiment, the present invention involves a process for the production of a homogenized pharmaceutical composition comprising the steps of growing, lysing and drying of keratinocyte cells, which process is characterized in that, immediately after lysing by a high-pressure homogenization, a mixture of xanthan gum and/or maltodextrin is added as a antiflocculant and/or antisedimentation agents to stabilize the keratinocyte cell lysate mixture.

In still another aspect of the present invention, disclosed herein are pharmaceutical compositions of cell lysate in the form of a solution or a suspension of the present invention obtainable by a process of the present invention.

In a particular embodiment of this aspect of the present invention, disclosed herein are pharmaceutical compositions of keratinocyte cell lysate in the form of a solution or suspension obtained by the process of the present invention. In further particular embodiments, a pharmaceutical composition comprising a keratinocyte cell lysate is in a freeze-dried or otherwise dried form.

In another particular embodiment of the present invention, disclosed herein is a method for treatment of wounds by administering a composition containing an efficient amount of cell lysate or fractions of cell lysates. Furthermore the composition can be administered via different carrier systems and drug dosage forms such as creams, ointments, gels, powders, sprays, solutions, suspensions, emulsions, lyophilized powders, aerosols.

In another particular embodiment of the present invention, disclosed herein is a composition of a cell lysate in the form of a solution or a suspension obtained by a process including forming a cell lysate in the form of a solution or a suspension, adding at least one anti-flocculant and/or at least one anti-sedimentation agent to the composition of a cell lysate in the form of a solution or suspension and stabilizing the composition of a cell lysate solution or suspension to which the at least one anti-flocculant and/or at least one anti-sedimentation agent has been added.

In a particular embodiment, disclosed herein is a composition of a cell lysate solution or suspension of the present invention obtainable by a process comprising the step of lysing the cells prior to adding at least one anti-flocculant and/or at least one anti-sedimentation agent to the composition of a non-viable cell lysate solution or suspension. One such method of lysing may be by high-pressure homogenization.

In a particular embodiment, disclosed herein is a composition of a cell lysate solution or suspension of the present invention obtainable by a process comprising the step of lysing the cells prior to adding xanthan gum at a concentration ranging from 0.001 to 5% w/v, more preferably 0.01 to 1% w/v, most preferably 0.05 to 0.5% w/v as a anti-flocculant and/or at least one anti-sedimentation agent to the composition of a non-viable cell lysate solution or suspension. One such method of lysing may be by high-pressure homogenization.

In a particular embodiment, disclosed herein is a composition of a cell lysate solution or suspension of the present invention obtainable by a process comprising the step of lysing the cells prior to adding a combination mixtures thereof of xanthan gum at a concentration ranging from 0.001 to 5% w/v, more preferably 0.01 to 1% w/v, most preferably 0.05 to 0.5% w/v and maltodextrin at concentration ranging from 0.01 to 10% w/v, more preferably 0.5 to 2% w/v as anti-flocculant and/or at least one anti-sedimentation agents to the composition of a non-viable cell lysate solution or suspension. One such method of lysing may be by high-pressure homogenization.

In another embodiment, the process for the production of a composition of cell lysate that is in the form of a solution or a suspension (possibly in a dried or freeze-dried form) of the present invention may be further comprised of sterilizing the composition of cell lysate following adding the xanthan gum thereto. Such sterilization may be performed chemically, by heat treatment (including the use of microwave energy) or by irradiation, such as UV, gamma or electron beam irradiation. In case of gamma or electron beam irradiation, the sterilization is performed preferably on the composition after drying (such as freeze-drying or spray drying), in order to minimize possible effects on the biological activity of the composition.

Having thus described the compositions of cell lysate of the present and the processes for their production, the following examples are now presented for the purposes of illustration only and are not meant to be, nor should they be, read as being restrictive.

Modifications of the compositions, processes, uses and methods disclosed above may be made without departing from the basic spirit of the invention. Accordingly, it will be appreciated by those skilled in the art that within the scope of the appended claims, the invention may be practiced other than has been specifically described herein.

EXAMPLES

Example 1

Culturing of Human Keratinocytes and Preparation of a Keratinocyte Cell Lysate

Keratinocytes are isolated from neonatal human foreskin. A foreskin specimen is incubated overnight at 4° C. in a solution containing 25 U/mL Dispase in order to obtain separation of epidermis and dermis. The epidermal part is collected and further processed by incubation for 30 minutes at 37° C. in a solution containing 0.05% trypsin and 0.02% EDTA in order to obtain single keratinocyte cells. The trypsin is then neutralized by adding a trypsin inhibitor and the cells are centrifuged, resuspended in a DMSO-containing cryopreservation solution and cryopreserved in liquid nitrogen.

After thawing, isolated keratinocytes are cultured using the 3T3 feeder fibroblast technique (Rheinwald J and Green H. Cell (1975) 6: 331-344: Serial cultivation of strains of human epidermal keratinocytes: the formation of keratinizing colonies from single cells) or in a commercially available low calcium keratinocyte medium.

After culturing, the cells are collected mechanically by scraping in an isotonic solution containing sodium chloride and phosphate buffer, homogenized mechanically and frozen at −70° C. After thawing the thus obtained crude lysate (Bulk Unprocessed Product) is supplemented with a lyoprotectant (sucrose) and citrate buffer and further processed by high pressure homogenization, using a cell breaker (Constant Systems, U.K). The resulting suspension (Bulk Formulated Lysate) is then filled in to vials and lyophilized.

Example 2

Use of Xanthan Gum and/or Maltodextrin to Prevent Flocculation and Sedimentation Unprocessed bulk lysate (BUP) was prepared as described in example 1. Formulated bulk product constituted 200 g of BUP (containing approx. 2 mg/ml of total protein) to which 13 g of sucrose powder was added This material was divided into three aliquots and processed as follows:

Aliquot IA was processed through a Constant Systems high-pressure homogenizer at 800 bar (one cycle). After processing, 12.5 ml of the homogenized material was supplemented with either:
1.25 ml of water (IA1)
0.33 ml of a 20% w/v solution of Lutrol F127 (IA2)
1.25 ml of a solution of 1% w/v xanthan gum/10% w/v maltodextrin (IA3)
1.25 ml of a solution of 1% w/v xanthan gum/10% w/v maltodextrin and 0.32 ml of a solution of 20% w/v Lutrol F127 (IA4)

Aliquot IB was processed through a Constant Systems high-pressure homogenizer at 2000 bar (one cycle). After processing, 12.5 ml of the homogenized material was supplemented with either:
1.25 ml of water (IB1)
0.33 ml of a 20% w/v solution of Lutrol F127 (IB2)
1.25 ml of a solution of 1% w/v xanthan gum/10% w/v maltodextrin (IB3)
1.25 ml of a solution of 1% w/v xanthan gum/10% w/v maltodextrin and 0.32 ml of a solution of 20% w/v Lutrol F127 (IB4)

Aliquot II was further subdivided into 4 aliquots of 25 ml which were first supplemented with either:
2.5 ml water (II1)
0.65 ml of a 20% w/v solution of Lutrol F127 (II2)
2.5 ml of a solution of 1% w/v xanthan gum/10% w/v maltodextrin (II3)
2.5 ml of a solution of 1% w/v xanthan gum/10% w/v maltodextrin and 0.65 ml of a solution of 20% w/v Lutrol F127 (II4).

These formulated samples were then passed through the high-pressure homogenizer at either 800 bar (II1A, II2A, II3A, II4A) or 2000 bar (II1B, II2B, II3B, II4B). The aliquots of processed formulated bulk product were filled into clear plastic 15-ml tubes, which were placed at 2-8° C. without disturbing. For this and all following examples, visual evaluation of flocculation or sedimentation was done at regular intervals, using a scoring system on a 0-5 scale (0/0=no flocculation/sedimentation, 5/5 is maximal flocculation/sedimentation, 5/0 is maximal flocculation, no sedimentation, etc.)

The results were evaluated after 2 hrs at 4° C. and are summarized in Table 1:

TABLE 1

| Reference | Homogenization pressure (bar) | Total protein concentration after homogenization (mg/ml) | Additives added before (B) or after (A) homogenization | Additives and concentration | Sedimentation test | Specific bioactivity (U/mg total protein) |
|---|---|---|---|---|---|---|
| IA1 | 800 | 1.8 | A | Water | 1/3 | 0.184 |
| IA2 | 800 | 1.8 | A | L 0.5% | 2/3 | — |
| IA3 | 800 | 1.8 | A | M 1%, X 0.1% | 0/0[1] | 0.288 |
| IA4 | 800 | 1.8 | A | M 1%, X 0.1%, L 0.5% | 1/0 | — |
| IB1 | 2000 | 1.8 | A | Water | 1/3 | 0.266 |
| IB2 | 2000 | 1.8 | A | L 0.5% | 2/3 | — |
| IB3 | 2000 | 1.8 | A | M, 1% X 0.1% | 0/0 | 0.430 |
| IB4 | 2000 | 1.8 | A | M 1%, X 0.1%, L 0.5% | 2/3[2] | — |
| II1A | 800 | 1.8 | B | Water | — | — |
| II1B | 2000 | 1.8 | B | Water | 1/2 | 0.266 |
| II2A | 800 | 1.8 | B | L 0.5% | — | — |
| II2B | 2000 | 1.8 | B | L 0.5% | — | — |
| II3A | 800 | 1.8 | B | M 1%, X 0.1% | 2/1 | 0.126 |
| II3B | 2000 | 1.8 | B | M 1%, X 0.1% | 3/2 | 0.260 |
| II4A | 800 | 1.8 | B | M 1%, X 0.1%, L 0.5% | — | — |
| II4B | 2000 | 1.8 | B | M 1%, X 0.1%, L 0.5% | — | — |

L = Lutrol F127;
M = maltodextrin;
X = xanthan gum;
[1]hardly any visible flakes, homogeneous and no sediment;
[2]possibly poor mixing of Lutrol-MX after homogenization This example shows that the combination of 1% maltodextrin and 0.1% xanthan gum suppresses the flocculation and sedimentation of lysate material. However, surprisingly this beneficial effect is observed only when the additives are added after, and not before, the high-pressure homogenization. Moreover, the addition of maltodextrin and xanthan gum does not negatively interfere with the biological activity of the lysate.

Example 3

Use of Xanthan Gum/Maltodextrin to Prevent Flocculation and Sedimentation of Concentrated Lysate Suspension Preparation of Unprocessed Bulk Lysate (BUP) was Done as Described in Example: 1.

Preparation of formulated bulk product was as follows:
1) To 105 ml BUP, 87.5 ml citrate buffer (120 mM, pH 6.8) was added:solution 1
2) To 128 ml of solution 1, 15 g of sucrose powder was added (solution 2)

Formulation A (no antiflocculant): 64 ml of solution 2 was processed through a Constant Systems homogenizer at 800 bar and then supplemented with 52 ml of water Formulation B (with antiflocculant): 64 ml of solution 2 was processed through a Constant Systems homogenizer at 800 bar and then supplemented with 29 ml of water and 23 ml of a solution containing 5% maltodextrin and 0.5% xanthan gum 3) Formulation C (with antiflocculant, no sucrose): 64 ml of solution 1 was processed through a Constant Systems homogenizer at 800 bar and then supplemented with 29 ml of water and 23 ml of a solution containing 5% maltodextrin and 0.5% xanthan gum After processing the samples were stored at 4° C. for 24 hrs and flocculation/sedimentation was scored using a 0-5 scale (0=no flocculation/sedimentation, 5=maximal flocculation/sedimentation). Samples were also lyophilized, treated by electron beam sterilization and evaluated for biological activity. Results are shown in Table 2:

TABLE 2

| Ref. | Formulation | Total protein concentration (mg/ml) | Sedimentation test 1.5 h | Sedimentation test 24 h | Bioassay (U/mg total protein) H | L | L + E |
|---|---|---|---|---|---|---|---|
| A | S/C | 1.12 | 0.5/1 | 0/2 | 0.121 | 0.157 | 0.106 |
| B | S/C/MX | 1.12 | 0.5/0 | 0.5/0 | 0.127 | 0.131 | 0.111 |
| C | C/MX | 1.12 | 0.5/0 | 1/0.5 | 0.136 | 0.199 | 0.131 |
| D | S/MX | 3.35 | 2/3 | 1/5 | — | — | — |

S: sucrose, 6.5%;
C: cirate 30 mM, pH 6.8;
M: maltodextrin 1%;
X: xanthan gum 0.1%;
H, after homogenization;
L: after lyophilization
L + E, after lyophilization and 31 kGy eletron beam irradiation.

These data indicate that the addition of 1% maltodextrin/0.1% xanthan gum in the presence of citrate buffer inhibits flocculation and sedimentation of a low concentration lysate for up to 24 hrs. However, when using a higher concentrated lysate and omitting the citrate buffer, significant flocculation and sedimentation is already evident at 1.5 hrs after homogenization. The data further confine that maltodextrin and xanthan gum do not negatively influence the bioactivity of the lysate and are compatible with electron beam irradiation (although the intrinsic bioactivity of the lysate is decreased by irradiation).

Example 4

Use of Xanthan Gum or Xanthan Gum/Maltodextrin to Prevent Flocculation and Sedimentation of Lysate Suspensions Containing Different Protein Concentrations Preparation of unprocessed bulk lysate (BUP) as described in example 1

Preparation of formulated bulk product:
1. Formulation 3XA and 3XB:

| | |
|---|---|
| BUP (approx. 0.98 mg/ml): | 94 g |
| 300 mM cirate buffer pH 6.8: | 20 g |
| Sucrose powder: | 13 g |
| Water: | 33 g |

Processing through high pressure homogenizer at 2000 bar

After processing the lysate was divided in two aliquots of 80 g to which either 20 g of a solution containing 5% maltodextrin/0.5% xanthan gum (Formulation 3XA) or 20 g of a solution containing 0.5% xanthan gum (formulation 3XB) was added.

2. Formulation 1XA and 1XB:

| | |
|---|---|
| BUP (approx. 0.98 mg/ml): | 30.3 g |
| 300 mM citrate buffer pH 6.8: | 20 g |
| Sucrose powder: | 13.2 g |
| Water: | 96.5 g |

Processing through high pressure homogenizer at 2000 bar

After processing the lysate was divided in two aliquots of 80 g to which either 20 g of a solution containing 5% maltodextrin/0.5% xanthan gum (formulation 1XA) or 20 g of a solution containing 0.5% xanthan gum (formulation 1XB) was added.

3. Formulation 0.3XA and 0.3XB:

Formulation 0.3XA is prepared by adding the following components to 25 g of formulation 1XA:

| | |
|---|---|
| sucrose: | 3.25 g |
| 300 mM citrate buffer pH 6.8: | 5 g |
| PBS buffer: | 31.75 g |
| 5% maltodextrin/0.5% xanthan gum: | 10 g |

Formulation 0.3XB is prepared by adding the following components to 25 g of formulation 1XB:

| | |
|---|---|
| sucrose: | 3.25 g |
| 300 mM citrate buffer pH 6.8: | 5 g |
| PBS buffer: | 31.75 g |
| 5% maltodextrin/0.5% xanthan gum: | 10 g |

The material was stored at 4° C. and evaluated for flocculation/sedimentation at different time points. The material was furthermore evaluated for biological activity. The results are summarized in Table 3:

TABLE 3

| Ref. | Additives added | Total protein concentration (mg/ml) | Sedimentation test 3 h | Sedimentation test 6 h | Sedimentation test 24 h | Bioassay (U/mg)* |
|---|---|---|---|---|---|---|
| 3XA | MXCS | 1.38 | 1/0 | 1/0 | 1/0 | 0.104 |
| 3XB | XCS | 1.38 | 1/0 | 1/0 | 1/0 | 0.081 |
| IXA | MXCS | 0.461 | 2/0 | 2/0 | 2/0 | 0.083 |
| 1XB | XCS | 0.461 | 1.5/0 | 2/0 | 2/0 | 0.07 |
| 0.3XA | MXCS | 0.138 | 2/0 | 2/0 | 1.5/0 | — |
| 0.3XB | XCS | 0.138 | 2/0 | 2/0 | 1.5/0 | |

*Due to unusually low bioactivity in this lysate preparation, bioassay results may be unreliable;
M: Maltodextrin 1%;
X: xanthan gum 0.1%;
C: citrate buffer 30 mM, pH 6.8;
S: sucrose: 6.5%

This example shows that at different final protein concentrations, xanthan gum alone has a comparable efficiency for preventing sedimentation and flocculation as the combination of maltodextrin and xanthan gum.

Example 5

Use of Xanthan Gum or Xanthan Gum/Maltodextrin to Prevent Flocculation and Sedimentation of Lysate Suspensions and Effect of Timing of Adding the Antiflocculants Preparation of unprocessed bulk lysate (BUP) as described in example 1

Preparation of formulated bulk product.

TABLE 4

| Ref. | Additives added | Total protein concentration (mg/ml) | Additive added before (B) or after (A) homogenization + time point of addition (min) | Sedimentation test 2 h | 3 h | 20 h | Bioassay (U/mg)* |
|---|---|---|---|---|---|---|---|
| A | MXC | 0.38 | A, 0' | 0.5/0 | 0.5/0 | 1/0 | 0.068 |
| B | XC | 0.38 | A, 0' | 0.5/0 | 0.5/0 | 1/0 | 0.084 |
| C | MXCS | 0.38 | A, 30' | 1/0 | 1/0 | 1.5/0 | 0.100 |
| D | XCS | 0.38 | A, 30' | 1/0 | 1/0 | 1.5/0 | 0.110 |
| E | MXCS | 0.38 | A, 5' | 1/0 | 1/0 | 1/0 | 0.089 |
| F | XCS | 0.38 | A, 5' | 1/0 | 1/0 | 1.5/0 | 0.078 |
| G | MXCS | 0.38 | A, 0' | 1/0 | 0.5/0 | 1/0 | 0.100 |
| H | XCS | 0.38 | A, 0' | 1/0 | 0.5/0 | 1/0 | 0.084 |
| I | MXCS | 0.38 | B | 1/1.5 | 2/2 | 1/3 | 0.105 |
| J | XCS | 0.38 | B | 1/1 | 2/2 | 1/3 | 0.078 |

*Due to unusually low bioactivity in this lysate preparation, bioassay results may be unreliable;
M: Maltodextrin 1%;
X: xanthan gum 0.1%;
C: citrate buffer 30 mM, pH 6.8;
S: sucrose: 6.5%

1. Formulation A and B (no sucrose):

| | |
|---|---|
| BUP (approx. 2.74 mg/ml): | 27.9 g |
| 300 mM citrate buffer pH 6.8: | 20 g |
| Water: | 112.1 g |

Homogenization through high pressure homogenizer at 2000 bar.

Homogenized material was divided over 2 aliquots of 80 g each to which either 20 g of a solution containing 5% maltodextrin/0.5% xanthan gum (formulation A) or 20 g of a solution containing 0.5 xanthan gum (formulation B) was added.

2. Formulations C-J (with sucrose):

| | |
|---|---|
| BUP (approx. 2.74 mg/ml): | 111.5 g |
| 300 mM citrate buffer pH 6.8: | 80 g |
| Sucrose powder: | 52.1 g |
| Water: | 398.1 g |

This mixture was divided over 8 aliquots of 80 g each.

Two aliquots were supplemented with either 20 g of a solution containing 5% maltodextrin/0.5% xanthan gum (formulation I) or 20 g of a solution containing 0.5 xanthan gum (formulation J) and subsequently processed through a high pressure homogenizer at 2000 bar.

Six aliquots were first processed through a high pressure homogenizer at 2000 bar and subsequently supplemented with antiflocculant additives either immediately after homogenization (formulations G, H) or at 5 minutes (formulations E, F) or 30 minutes (formulations C, D) after homogenization. The additives used were either 20 g of a solution containing 5% maltodextrin/0.5% xanthan gum (formulations C, E, G) or 20 g of a solution containing 0.5% xanthan gum (formulations D, F, H).

The processed samples were stored at 4° C. and evaluated for flocculation/sedimentation using a 0-5 score. Samples were also tested for biological activity. The results are summarized in Table 4:

This example shows that xanthan gum has a similar efficacy for inhibiting flocculation and sedimentation of the lysate suspension as the combination maltodextrin/xanthan gum. It also confirms the surprising finding that the addition of the antiflocculant needs to occur after the high pressure homogenization step in order to be effective. Addition of the antiflocculant is preferably done as soon as possible after the homogenization in order to minimize subsequent flocculation.

Example 6

Use of Xanthan Gum, Maltodextrin or Xanthan Gum/Maltodextrin to Prevent Flocculation and Sedimentation of Lysate Suspensions and Effect of Addition Before or After Homogenization Preparation of unprocessed bulk lysate (BUP) as described in example 1

Preparation of formulated bulk product was done by addition of sucrose to a final concentration of 6.5% (formulations 1,2,3) or maltodextrin to a concentration of 5% (formulation 4,5). The suspension was subsequently homogenized at a pressure of 800 bar and supplemented with either (percentages refer to final concentrations:):

Formulation 1: Maltodextrin 1%, xanthin gum 0.1%

Formulation 2: Maltodextrin 1%

Formulation 3: Xanthan gum 0.1%

Formulation 4: No additive

Formulation 5: Xanthan gum 0.1%

After processing the material was stored at 4° C. and evaluated for flocculation/sedimentation at different time points. The results are summarized in Table 5:

TABLE 5

| Ref. | Formulation (%) | Addition of maltodextrin before (B) or after (A) homogenization | Addition of xanthan gum before (B) or after (A) homogenization | Sedimentation test 2.5 h | 4 h | 20 h |
|---|---|---|---|---|---|---|
| 1 | M (1), X (0.1), S (6.5) | A | A | 0/0 | 0/0 | 1/0 |
| 2 | M (1), S (6.5) | A | — | 0/2 | 0/2 | 0/3 |
| 3 | X (0.1), S (6.5) | — | A | 1/0 | 1/0 | 1/2 |
| 4 | M (5) | B | — | 1/0 | 0/1 | 1/2 |
| 5 | M (5), X (0.1) | B | A | 1/0 | 2/0 | 3/3 |

M: Maltodextrin 1% or 5%;
X: xanthan gum 0.1%;
S: sucrose: 6.5%

This example shows that the combination of maltodextrin and xanthan gum is more effective at inhibiting flocculation than xanthan gum alone. Use of maltodextrin alone causes a limited inhibition of flocculation but does not inhibit sedimentation over a longer time period.

Example 7

Use of Xanthan Gum/Maltodextrin to Prevent Flocculation and Sedimentation of Lysate Suspensions of Different Concentrations in the Presence or Absence of Sucrose Preparation of Unprocessed Bulk Lysate (BUP) was done as Described in Example 1
Preparation of formulated bulk product
1. Formulation A and B (sucrose):

| | |
|---|---|
| BUP (approx. 3.1 mg/ml): | 30 ml |
| 150 mM citrate buffer pH 6.8: | 20 ml |
| Sucrose powder: | 6.5 g |

Homogenization through high pressure homogenizer at 800 bar.
Homogenized material was divided over 2 aliquots of 25 ml each to which either 25 ml water (formulation A) or 15 ml water and 10 ml of a solution containing 5% maltodextrin/0.5% xanthan gum (formulation B) was added.
2. Formulation C (no sucrose):

| | |
|---|---|
| BUP (approx. 3.1 mg/ml): | 15 ml |
| 150 mM citrate buffer pH 6.8: | 10 ml |

Homogenization through high pressure homogenizer at 800 bar.
To the homogenized material 15 ml water and 10 ml of a solution containing 5% maltodextrin/0.5% xanthan gum (formulation B) was added.
3. Formulation D (higher protein concentration, no citrate buffer):

| | |
|---|---|
| BUP (approx. 3.1 mg/ml): | 45 ml |
| Sucrose powder: | 3.7 g |

Homogenization through high pressure homogenizer at 800 bar.
To the homogenized material 12 ml of a solution containing 5% maltodextrin/0.5% xanthan gum (formulation B) was added.
The samples were stored at 4° C. and evaluated for flocculation and sedimentation at different time points and tested for biological activity. The results are summarized in Table 6:

TABLE 6

| Ref. | Formulation | Total protein concentration (mg/ml) | Sedimentation test 4 h | 23 h | 96 h | Bioassay (U/mg) |
|---|---|---|---|---|---|---|
| A | CS | 0.92 | 0/1.5 | 0/2 | 0/3 | 0.127 |
| B | MXCS | 0.92 | 0/0 | 0/0.5 | 1/1 | 0.148 |
| C | MXC | 0.92 | 1/0 | 0/2 | 1/1 | 0.144 |
| D | MXCS | 2.4 | 0.5/0 | 0/0.5 | 2/2 | — |

M: Maltodextrin 1%;
X: xanthan gum 0.1%;
C: citrate buffer 30 mM, pH 6.8;
S: sucrose 6.5%

This example shows that the combination maltodextrin 1%/xanthan gum 0.1% significantly inhibits both flocculation and sedimentation of the lysate up to at least 23 hours after homogenization. The presence of sucrose slightly improves the effect of maltodextrin/xanthan gum. After longer incubation (96 hrs), sedimentation and flocculation occurs even in presence of maltodextrin/xanthan gum, especially at higher protein concentrations. The presence of maltodextrin and xanthan gum does not affect the biological activity of the lysate.

The invention claimed is:
1. A method of promoting wound healing comprising applying a pharmaceutical composition comprising a homogeneous, total keratinocyte lysate and 0.001-1 w/v % xanthan gum as an antiflocculant and/or antisedimentation agent to an area of skin in need of said promoting.
2. The method of claim 1 wherein said wound is at least one of a wound and a skin ulcer.
3. The method of claim 1 wherein said composition is in the form of a dry powder, a freeze-dried form, a suspension or a solution.
4. The method of claim 1 wherein said composition is in the form of a gel, a cream, an ointment or a biocompatible matrix.

5. The method of claim 1 wherein said composition further comprises maltodextrin.

6. The method of claim 1, wherein said composition further comprises a buffering agent.

7. The method of claim 1, wherein said composition further comprises at least one of a pharmaceutically acceptable carrier, excipient or vehicle.

8. The method of claim 1 wherein said composition further comprises a pharmaceutically acceptable vehicle.

9. The method of claim 7 wherein said pharmaceutically acceptable vehicle is a dry powder, a suspension or a solution.

10. The method of claim 7 wherein said pharmaceutically acceptable vehicle is a gel, cream, ointment or a biocompatible matrix.

\* \* \* \* \*